(12) United States Patent
Song et al.

(10) Patent No.: US 7,282,200 B2
(45) Date of Patent: *Oct. 16, 2007

(54) MIXED-CELL GENE THERAPY

(75) Inventors: Sun Uk Song, Inchon (KR); Youngsuk Yi, Gaithersburg, MD (US); Kwan Hee Lee, Gaithersburg, MD (US); Moon Jong Noh, Gaithersburg, MD (US)

(73) Assignee: Tissuegene, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/303,547

(22) Filed: Dec. 16, 2005

(65) Prior Publication Data

US 2006/0115463 A1 Jun. 1, 2006

Related U.S. Application Data

(63) Continuation of application No. 10/382,137, filed on Mar. 5, 2003, now Pat. No. 7,005,127.

(60) Provisional application No. 60/369,162, filed on Mar. 29, 2002.

(51) Int. Cl.
*A61K 48/00* (2006.01)
*C12N 5/10* (2006.01)

(52) U.S. Cl. ............... 424/93.21; 424/93.1; 424/93.2; 435/347; 514/44

(58) Field of Classification Search ............. None
See application file for complete search history.

(56) References Cited

U.S. PATENT DOCUMENTS

| | | | |
|---|---|---|---|
| 5,700,774 A | 12/1997 | Hattersley et al. | |
| 5,766,585 A | 6/1998 | Evans et al. | |
| 5,842,477 A | 12/1998 | Naughton et al. | |
| 5,846,931 A | 12/1998 | Hattersley et al. | |
| 5,858,355 A | 1/1999 | Glorioso et al. | |
| 6,315,992 B1 | 11/2001 | Noh et al. | |
| 6,413,511 B1 | 7/2002 | Glorioso et al. | |
| 6,797,703 B1 | 9/2004 | Noh et al. | |
| 7,005,127 B2 * | 2/2006 | Song et al. | 424/93.21 |

FOREIGN PATENT DOCUMENTS

| | | | |
|---|---|---|---|
| WO | WO 96/39196 A1 | 12/1996 | |
| WO | WO 00/66177 A1 | 11/2000 | |
| WO | WO 01/34166 A1 | 5/2001 | |
| WO | WO 03/082302 A2 | 10/2003 | |

OTHER PUBLICATIONS

Brittberg et al, Oct. 6, New Eng. J. Med 331(14): 889-895, 1994.*
Valcourt et al, Sep. 15, Exp. Cell Res. 251: 264-274, 1999.*
Chang et al., December, Endocrine Rev. 23: 787-823, 2002.*
Fukui et al., December, Curr. Rheumatol. Rep. 3: 496-505, 2001.*
Bakker et al., February, Osteoarthritis and Cartilage 9(2): 128-136, 2001.*
van Beuningen et al, January, Osteoarthritis and Cartilage 8(1): 25-33, 2000.*
Evans et al., February, Gene Therapy 11(4): 379-389, 2004.*
Evans et al., February, Curr. Rheumatol. Rep. 6(1): 31-40, 2004.*
Goomer et al, April, Osteoarthritis Cartilage 9(3): 248-256, 2001.*
Lee et al, Iowa Orthop J. 20: 11-16, 2000. Abstract only.*
Goomer et al, Osteoarthritis and Cartilage 9:248-256, 2001.*
Lee et al, Iowa Orthop J. 20: 11-6, 2000.*
Song et al., "Hyaline Cartilage Regeneration Using Mixed Human Chondrocytes and Transforming Growth Factor-Beta1-Producing Chondrocytes," Tissue Engineering 11(9/10):1516-1526 (2005).
Lee et al, "Regeneration of Hyaline Cartilage by Cell-Mediated Gene Therapy Using Transforming Growth Factor Beta1-Producing Fibroblasts", Human Gene Therapy, vol. 12, pp. 1805-1813 (2001).
Groomer et al. "High-efficiency non-viral transfection of primary chondrocytes and perichondrial cells for ex-vivo gene therapy to repair articular cartilage defects", Osteoarthritis Cartilage. Apr. 2001;9(3):248-56.
Van Beuningen et al. "Osteoarthritis-like changes in the murine knee joint resulting from intra-articular transforming growth factor-beta injections", Osteoarthritis Cartilage. Jan. 2000;8(1):25-33.

(Continued)

*Primary Examiner*—Q. Janice Li
*Assistant Examiner*—Kevin K. Hill
(74) *Attorney, Agent, or Firm*—Joseph Hyosuk Kim; JHK Law

(57) ABSTRACT

The subject invention is directed to a mixed cell composition to generate a therapeutic protein at a target site by providing a first population of mammalian cells transfected or transduced with a gene that is sought to be expressed, and a second population of mammalian cells that have not been transfected or transduced with the gene, wherein endogenously existing forms of the second population of mammalian cells are decreased at the target site, and wherein generation of the therapeutic protein by the first population of mammalian cells at the target site stimulates the second population cells to induce a therapeutic effect.

17 Claims, 8 Drawing Sheets

OTHER PUBLICATIONS

Bakker et al. "Overexpression of active TGF-beta-1 in the murine knee joint: evidence for synovial-layer-dependent chondro-osteophyte formation", Osteoarthritis Cartilage. Feb. 2001;9(2):128-36.

Brittberg et al. "Treatment of deep cartilage defects in the knee with autologous chondrocyte transplantation", N Engl J Med. Oct. 6, 1994;331(14):889-95.

Valcourt et al. "Different effects of born morphogenetic proteins 2, 4, 12, and 13 on the expression of cartilage and bone markers in the MC615 chondrocyte cell line", Exp Cell Res. Sep. 15, 1999:251(2):264-74.

Fukui et al. "Cell biology of osteoarthritis: the chondrocyte's response to injury", Curr Rheumatol Rep. Dec. 2001;3(6):496-505.

Evans et al. "Osteoarthritis gene therapy", Gene Ther. Feb. 2004;11(4):379-89.

Evans, C.H. "Gene therapies for osteoarthritis", Curr Rheumatol Rep. Feb. 2004;6(1):31-40.

Chang et al. "Genetic analysis of the mammalian transforming growth factor-beta superfamily", Endocr Rev. Dec. 2002;23(6):787-823.

* cited by examiner hChon+3T3-TGF β1
(6 wk)

Control
(6 wk)

hChon+3T3-hBMP-2
(6 wk)

Control
(6 wk)

MIXED-CELL GENE THERAPY

This application is a continuation of application Ser. No. 10/382,137, filed Mar. 5, 2003, now U.S. Pat. No. 7,005,127, which claims benefit of the provisional application 60/369,162, filed Mar. 29, 2002.

BACKGROUND OF THE INVENTION

1. Field of the Invention

The present invention relates to using a mixture of cells for somatic cell gene therapy. The present invention also relates to a mixture of cells that include connective tissue cells transfected or transduced with a gene encoding a member of the transforming growth factor β superfamily and connective tissue cells that have not been transfected or transduced with a gene encoding a member of the transforming growth factor β superfamily. The present invention also relates to a method of regenerating cartilage by injecting the cell mixture to a mammalian connective tissue. In addition, the present invention relates to a method of treating osteoarthritis by injecting the cell mixture to a mammalian connective tissue.

2. Brief Description of the Related Art

In the orthopedic field, degenerative arthritis or osteoarthritis is the most frequently encountered disease associated with cartilage damage. Almost every joint in the body, such as the knee, the hip, the shoulder, and even the wrist, is affected. The pathogenesis of this disease is the degeneration of hyaline articular cartilage (Mankin et al., J Bone Joint Surg, 52A: 460-466, 1982). The hyaline cartilage of the joint becomes deformed, fibrillated, and eventually excavated. If the degenerated cartilage could somehow be regenerated, most patients would be able to enjoy their lives without debilitating pain.

Traditional routes of drug delivery, such as oral, intravenous or intramuscular administration, to carry the drug to the joint are inefficient. The half-life of drugs injected intraarticularly is generally short. Another disadvantage of intraarticular injection of drugs is that frequent repeated injections are necessary to obtain acceptable drug levels at the joint spaces for treating a chronic condition such as arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as gastrointestinal upset and changes in the hematological, cardiovascular, hepatic and renal systems of the mammalian host.

In the orthopedic field, some cytokines have been considered as candidates for the treatment of orthopedic diseases. Bone morphogenic protein has been considered to be an effective stimulator of bone formation (Ozkaynak et al., EMBO J, 9:2085-2093, 1990; Sampath and Rueger, Complications in Ortho, 101-107, 1994), and TGF-β has been reported as a stimulator of osteogenesis and chondrogenesis (Joyce et al., J Cell Biology, 110:2195-2207, 1990).

Transforming growth factor-β (TGF-β) is considered to be a multifunctional cytokine (Sporn and Roberts, Nature (London), 332: 217-219, 1988), and plays a regulatory role in cellular growth, differentiation and extracellular matrix protein synthesis (Madri et al., J Cell Biology, 106: 1375-1384, 1988). TGF-β inhibits the growth of epithelial cells and osteoclast-like cells in vitro (Chenu et al., Proc Natl Acad Sci, 85: 5683-5687, 1988), but it stimulates enchondral ossification and eventually bone formation in vivo (Critchlow et al., Bone, 521-527, 1995; Lind et al., A Orthop Scand, 64(5): 553-556, 1993; and Matsumoto et al., In vivo, 8: 215-220, 1994). TGF-β-induced bone formation is mediated by its stimulation of the subperiosteal pluripotential cells, which eventually differentiate into cartilage-forming cells (Joyce et al., J Cell Biology, 110: 2195-2207, 1990; and Miettinen et al., J Cell Biology, 127-6: 2021-2036, 1994).

The biological effect of TGF-β in orthopedics has been reported (Andrew et al., Calcif Tissue In. 52: 74-78, 1993; Borque et al., Int J Dev Biol., 37:573-579, 1993; Carrington et al., J Cell Biology, 107:1969-1975, 1988; Lind et al., A Orthop Scand. 64(5):553-556, 1993; Matsumoto et al., In vivo, 8:215-220, 1994). In mouse embryos, staining shows that TGF-β is closely associated with tissues derived from the mesenchyme, such as connective tissue, cartilage and bone. In addition to embryologic findings, TGF-β is present at the site of bone formation and cartilage formation. It can also enhance fracture healing in rabbit tibiae. Recently, the therapeutic value of TGF-β has been reported (Critchlow et al., Bone, 521-527, 1995; and Lind et al., A Orthop Scand, 64(5): 553-556, 1993), but its short-term effects and high cost have limited wide clinical application.

Intraarticular injection of TGF-β for the treatment of arthritis is not desirable, because the injected TGF-β has a short duration of action, as TGF-β is degraded into inactive form in vivo. Therefore, a new method for long-term release of TGF-β is necessary for the regeneration of hyaline cartilage.

There have been reports of regeneration of articular cartilage with autotransplantation of cartilage cells (Brittberg et al., New Engl J Med 331: 889-895, 1994), but this procedure entails two operations with wide excision of soft tissues. If intraarticular injection is enough for the treatment of degenerative arthritis, it will be of great economic and physical benefit to the patients.

Gene therapy, which is a method of transferring a specific protein to a specific site, may be the answer to this problem (Wolff and Lederberg, Gene Therapeutics ed. Jon A. Wolff, 3-25, 1994; and Jenks, J Natl Cancer Inst, 89(16): 1182-1184, 1997).

U.S. Pat. Nos. 5,858,355 and 5,766,585 disclose making a viral or plasmid construct of the IRAP (interleukin-1 receptor antagonist protein) gene; transfecting synovial cells (U.S. Pat. No. 5,858,355) and bone marrow cells (U.S. Pat. No. 5,766,585) with the construct; and injecting the transfected cells into a rabbit joint, but there is no disclosure of using a gene belonging to the TGF-β superfamily to regenerate connective tissue.

U.S. Pat. Nos. 5,846,931 and 5,700,774 disclose injecting a composition that includes a bone morphogenesis protein (BMP), which belongs to the TGF β "superfamily", together with a truncated parathyroid hormone related peptide to effect the maintenance of cartilaginous tissue formation, and induction of cartilaginous tissue. However, there is no disclosure of a gene therapy method using the BMP gene.

U.S. Pat. No. 5,842,477 discloses implanting a combination of a scaffolding, periosteal/perichondrial tissue, and stromal cells, including chondrocytes, to a cartilage defected area. Since this patent disclosure requires that all three of these elements be present in the implanted system, the reference fails to disclose or suggest the simple gene therapy method of the invention which does not require the implantation of the scaffolding or the periosteal/perichondrial tissue.

U.S. Pat. No. 6,315,992 discloses that hyaline cartilage is generated in defected mammalian joint when fibroblast cells transfected with TGF-β1 are injected into the defected knee joint. However, the patent does not disclose the advantages of using a mixed cell composition as in the present invention.

Lee et al. Human Gene Therapy, 12: 1085-1813, 2001 discloses that hyaline cartilage is generated in defected mammalian joint when fibroblast cells transfected with TGF-β1 are injected into the defected knee joint. However, Lee et al. does not disclose using a mixed cell composition as in the present invention.

In spite of these prior art disclosures, there remains a very real and substantial need for a more effective and potent treatment method to not only regenerate connective tissue in the mammalian host, but also better and more effective somatic cell gene therapy methods as well.

SUMMARY OF THE INVENTION

The present invention has met the herein before described need.

The presently claimed invention is directed to a mixed cell composition that is used to generate a therapeutic protein at a target site, comprising: a) a first population of mammalian cells transfected or transduced with a gene that is sought to be expressed; b) a second population of mammalian cells that have not been transfected or transduced with the gene, wherein endogenously existing forms of the second population of mammalian cells are decreased at the target site, and wherein generation of the therapeutic protein by the first population of mammalian cells at the target site stimulates the second population cells to induce a therapeutic effect; and c) a pharmaceutically acceptable carrier thereof.

In the claimed invention, the mixed cell composition may be in an injectable composition.

The claimed invention is further directed to a mixed cell composition that includes a hyaline cartilage-generating effective amount of: a) a first population of fibroblast or chondrocyte cells transfected or transduced with a gene encoding transforming growth factor β (TGF-β) or bone morphogenetic protein (BMP); b) a second population of fibroblast or chondrocyte cells that have not been transfected or transduced with a gene encoding TGF-β or BMP; and c) a pharmaceutically acceptable carrier thereof.

In a more specific embodiment, the claimed invention is directed to a mixed cell composition that comprises hyaline cartilage-generating effective amount of: a) a first population of fibroblast cells transfected or transduced with a gene encoding TGF-β or BMP; b) a second population of chondrocyte cells that have not been transfected or transduced with a gene encoding TGF-β or BMP; and c) a pharmaceutically acceptable carrier thereof.

In the composition above, the composition may comprise a hyaline cartilage-generating effective amount of: a) a first population of chondrocyte cells transfected or transduced with a gene encoding TGF-β or BMP; b) a second population of chondrocyte cells that have not been transfected or transduced with a gene encoding TGF-β or BMP; and c) a pharmaceutically acceptable carrier thereof.

In the composition above, the gene may be, but not limited to, TGF-β1, TGF-β2, TGF-β3, BMP-2, BMP-3, BMP4, BMP-5, BMP-6, BMP-7 or BMP-9. In particular, the gene may be TGF-β1 or BMP-2.

Furthermore, in the composition, the ratio of the second population of fibroblast or chondrocyte cells that have not been transfected or transduced with a gene encoding TGF-β or BMP to the first population of fibroblast or chondrocyte cells that have been transfected or transduced with a gene encoding TGF-β or BMP is from about 1-20 to 1. In particular, ratio may be from about 1-10 to 1, and further, about 1-3 to 1.

In the composition above, the first population of cells transfected or transduced with a gene may be irradiated. And in particular, the first population of fibroblast or chondrocyte cells transfected or transduced with a gene encoding TGF-β or BMP is irradiated.

The cells of the mixed population of cells may be derived from the same source organism. In particular, in certain embodiments, the first population of fibroblast or chondrocyte cells transfected or transduced with a gene encoding TGF-β or BMP and the second population of fibroblast or chondrocyte cells not transfected or transduced with a gene encoding TGF-β or BMP are derived from the same source organism.

The cells of the mixed population of cells may be derived from different source organisms. In particular, in certain embodiments, the first population of fibroblast or chondrocyte cells transfected or transduced with a gene encoding TGF-β or BMP and the second population of fibroblast or chondrocyte cells not transfected or transduced with a gene encoding TGF-β or BMP are derived from different source organisms. The first population of cells and the second population of cells may be derived from different source mammals. And in particular, the first population of fibroblast or chondrocyte cells transfected or transduced with a gene encoding TGF-β or BMP and the second population of fibroblast or chondrocyte cells not transfected or transduced with a gene encoding TGF-β or BMP are derived from different source mammals.

The presently claimed invention is also directed to a method of generating a therapeutic protein at a target site in a mammal comprising: a) generating a recombinant vector comprising a DNA sequence encoding the therapeutic protein operatively linked to a promoter; b) transfecting or transducing a population of cells in vitro with said recombinant vector; and c) injecting a mixed cell composition comprising protein generating effective amount of (i) a first population of cells transfected or transduced with the gene; (ii) a second population of cells that have not been transfected or transduced with the gene; and (iii) a pharmaceutically acceptable carrier thereof, into the target site, wherein endogenously existing forms of the second population of mammalian cells are decreased at the target site, and wherein generation of the therapeutic protein by the first population of mammalian cells at the target site stimulates the second population cells to induce a therapeutic effect.

In particular, according to the above method, a method is provided for generating hyaline cartilage in a mammal comprising: a) generating a recombinant vector comprising a DNA sequence encoding transforming growth factor β (TGF-β) or bone morphogenic protein (BMP) operatively linked to a promoter; b) transfecting or transducing a population of fibroblast or chondrocyte cells in vitro with said recombinant vector; and c) injecting an injectable mixed cell composition comprising hyaline cartilage-generating effective amount of (i) a first population of fibroblast or chondrocyte cells transfected or transduced with a gene encoding TGF-β or BMP; (ii) a second population of fibroblast or chondrocyte cells that have not been transfected or transduced with a gene encoding TGF-β or BMP; and (iii) a pharmaceutically acceptable carrier thereof, into a joint space of a mammal such that expression of the DNA sequence encoding TGF-β or BMP within the joint space occurs resulting in the generation of hyaline cartilage in the joint space.

According to the above method, the gene may be, but not limited to, TGF-β1, TGF-β2, TGF-β3, BMP-2, BMP-3, BMP-4, BMP-5, BMP-6, or BMP-7. In particular, the gene may be TGF-β1 or BMP-2.

Furthermore, the method may encompass mixing the cells in a ratio according to the following: the second population of fibroblast or chondrocyte cells that have not been transfected or transduced with a gene encoding TGF-β or BMP to the first population of fibroblast or chondrocyte cells that have been transfected or transduced with a gene encoding TGF-β or BMP may be from about 3-20 to 1. The ratio may be from about 3-10 to 1. Still further, the ratio may be from about 10 to 1.

The claimed invention also provides that in the above method, the first population of fibroblast or chondrocyte cells transfected or transduced with a gene encoding TGF-β or BMP is irradiated.

With regard to the source of the cells in the method described above, the first population of fibroblast or chondrocyte cells transfected or transduced with the gene encoding TGF-β or BMP and the second population of fibroblast or chondrocyte cells not transfected or transduced with a gene encoding TGF-β or BMP are syngeneic, allogeneic, or xenogeneic with respect to the host recipient.

The method described above may use a recombinant vector such as a viral vector. The recombinant vector may be, but not limited to, a plasmid vector. In addition, the transfection or transduction may be accomplished by liposome encapsulation, calcium phosphate coprecipitation, electroporation, DEAE-dextran mediation or virus mediation.

In the practice of the claimed invention, cells may be stored prior to transplantation. And the cells may be stored in a cryopreservative prior to transplantation.

In another embodiment, the present invention is directed to a method of treating osteoarthritis comprising: a) generating a recombinant vector comprising a DNA sequence encoding transforming growth factor β (TGF-β) or bone morphogenic protein (BMP) operatively linked to a promoter; b) transfecting or transducing a population of fibroblast or chondrocyte cells in vitro with said recombinant vector; and c) injecting an injectable mixed cell composition comprising hyaline cartilage-generating and osteoarthritis treating effective amount of, (i) a first population of fibroblast or chondrocyte cells transfected or transduced with a gene encoding TGF-β or BMP; (ii) a second population of fibroblast or chondrocyte cells that have not been transfected or transduced with a gene encoding TGF-β or BMP; and (iii) a pharmaceutically acceptable carrier thereof that is not a non-living three dimensional structure into a joint space of a mammal such that expression of the DNA sequence encoding TGF-β or BMP within the joint space occurs resulting in the generation of bone and cartilage tissue in the joint space.

The present invention is further directed to an injectable mixed cell composition comprising hyaline cartilage-generating effective and osteoarthritis treating amount of: a) a first population of fibroblast or chondrocyte cells transfected or transduced with a gene encoding transforming growth factor β (TGF-β) or bone morphogenic protein (BMP); b) a second population of fibroblast or chondrocyte cells that have not been transfected or transduced with a gene encoding TGF-β or BMP; and c) a pharmaceutically acceptable carrier thereof.

In a another embodiment of the claimed invention, the presently claimed invention provides for a storage container for storing cells at a temperature of about −70° C. to about −196° C., comprising a mixed cell composition to generate a protein at a site of interest, comprising: a) a first population of mammalian cells transfected or transduced with a gene that is sought to be expressed; b) a second population of mammalian cells that have not been transfected or transduced with the gene, wherein endogenously existing forms of the second population of mammalian cells are decreased at the target site, and wherein generation of the therapeutic protein by the first population of mammalian cells at the target site stimulates the second population cells to induce a therapeutic effect; and c) a pharmaceutically acceptable carrier thereof.

In particular, the present application provides for a storage container for storing cells at a temperature of about −70° C. to about −196° C., comprising an injectable mixed cell composition comprising hyaline cartilage-generating effective amount of: a) a population of fibroblast or chondrocyte cells transfected or transduced with a gene encoding TGF-β or BMP; b) a population of fibroblast or chondrocyte cells that have not been transfected or transduced with a gene encoding TGF-β or BMP; and c) a pharmaceutically acceptable carrier thereof.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 2A and 2B show control NIH3T3-methallothionein (A) and NIH3T3-BMP2 cells (B). Blue color in panel (B) shows expression of BMP2 protein.

FIGS. 3A and 3C show pictures of the femoral condyles 6 weeks post injection with either a mixture of hChon (human chondrocytes) and NIH3T3-TGF-β1 cells (A) or hChon alone (C). FIGS. 3B and 3D show Mason's trichrome staining of sections from the femoral condyle injected with either a mixture of hChon and NIH3T3-TGF-β1 cells (B) or hChon alone (D). Original magnification: (B & D)×12.5].

FIGS. 4A and 4D show pictures of the femoral condyles 12 weeks post injection with either a mixture of hChon and NIH3T3-TGF-β1 cells (A) or hChon alone (D). FIGS. 4B and 4E show Mason's trichrome staining, and FIG. 4C shows Safranin-O staining of sections from the femoral condyle injected with either a mixture of hChon and NIH3T3-TGF-β1 cells (B & C) or hChon alone (E). Original magnification: (B, C & E)×12.5.

FIGS. 5A and 5C show pictures of the femoral condyles 6 weeks post injection with either a mixture of hChon and NIH3T3-BMP-2 cells (A) or hChon alone (C). FIGS. 5B and 5D show Mason's trichrome staining of sections from the femoral condyle injected with either a mixture of hChon and NIH3T3-BMP-2 cells (B) or hChon alone (D). Original magnification: (B & D)×12.5.

FIGS. 6A and 6D show pictures of the femoral condyles 12 weeks post injection with either a mixture of hChon and NIH3T3-BMP-2 cells (A) or hChon alone (D). FIGS. 6B and 6E show Mason's trichrome staining and FIG. 6C shows Safranin-O staining of sections from the femoral condyle injected with either mixture of hChon and NIH3T3-BMP-2 cells (B & C) or hChon alone (E). Original magnification: (B, C & E)×12.5.

FIGS. 7A and 7C show pictures of the femoral condyles 6 weeks post injection with either a mixture of hChon and hChon-TGF-β1 cells (A) or hChon alone (C). FIGS. 7B and 7D show Mason's trichrome staining of sections from the femoral condyle injected with either mixture of hChon and hChon-TGF-β1 cells (B) or hChon alone (D). [Original magnification: (B& D)×12.5].

FIGS. 8A and 8C show pictures of the femoral condyles 6 weeks post injection with a mixture of hChon and hChon-TGF-β1 cells (3:1 ratio) (A) or a mixture of hChon and hChon-TGF-β1 cells (5:1 ratio) (C). FIGS. 8B and 8D show Mason's trichrome staining of sections from the femoral condyle injected with a mixture of hChon and hChon-TGF-β1 cells with 3:1 ratio (B) or 5:1 (D). [Original magnification: (B& D)×12.5].

DETAILED DESCRIPTION OF THE INVENTION

Figure 1:
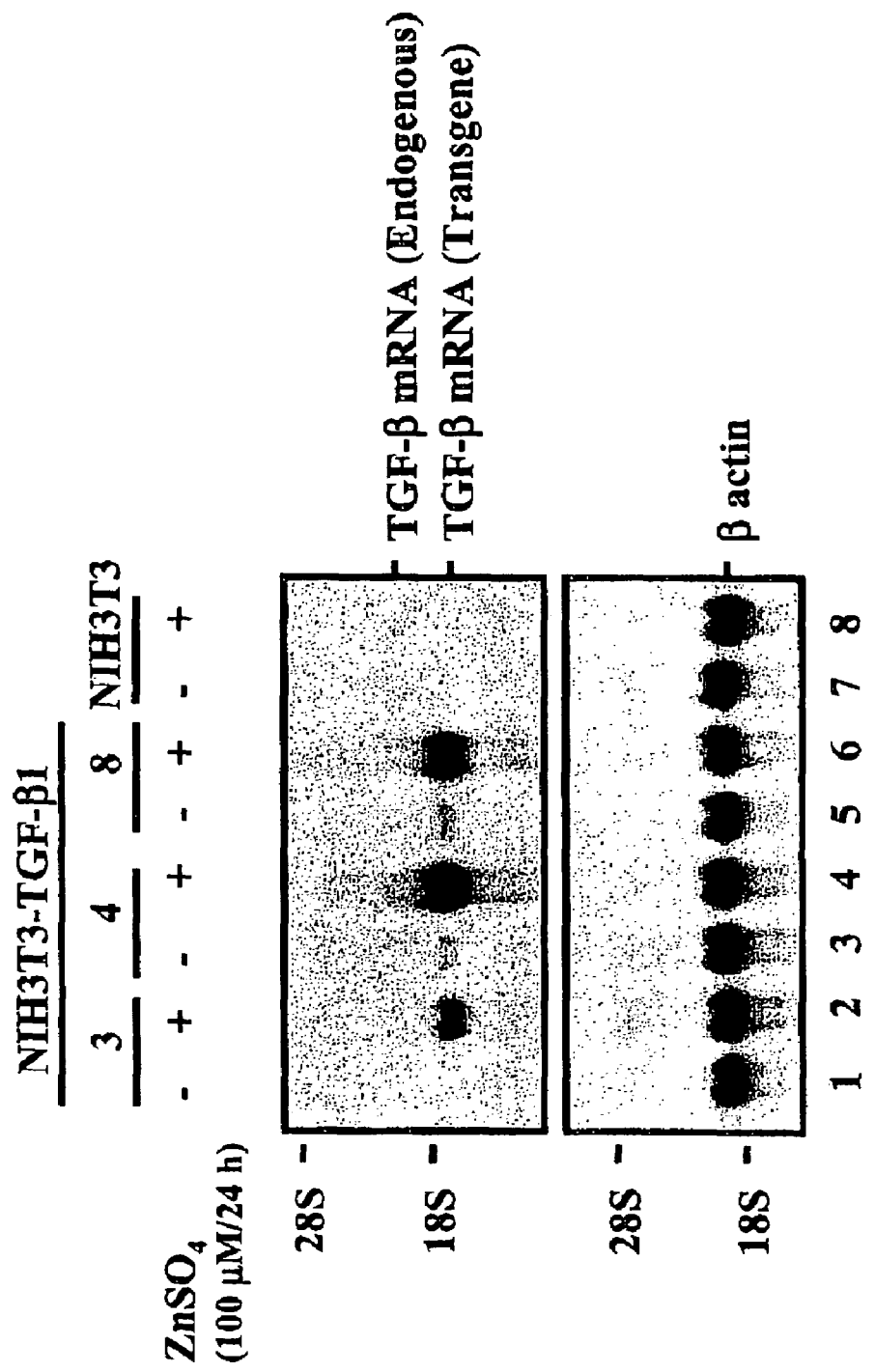
FIG. 1 shows expression of TGF-β1 mRNA. Total RNA was isolated from NIH 3T3 cells or NIH 3T3 cells stably transfected with pmTβ1, a TGF-β1 expression vector, which were grown in the absence or presence of zinc. Total RNA (15 mg) was probed with either the TGF-β1 cDNA or β actin cDNA as a control.

As used herein, the term "patient" includes members of the animal kingdom including but not limited to human beings.

As used herein, the term "mammalian host" includes members of the animal kingdom including but not limited to human beings.

As used herein, the term "connective tissue" is any tissue that connects and supports other tissues or organs, and includes but is not limited to a ligament, a cartilage, a tendon, a bone, and a synovium of a mammalian host.

As used herein, the terms "connective tissue cell" and "cell of a connective tissue" include cells that are found in the connective tissue, such as fibroblasts, cartilage cells (chondrocytes), and bone cells (osteoblasts/osteocytes), which secrete collagenous extracellular matrix, as well as fat cells (adipocytes) and smooth muscle cells. Preferably, the connective tissue cells are fibroblasts, cartilage cells, and bone cells. It will be recognized that the invention can be practiced with a mixed culture of connective tissue cells, as well as cells of a single type. It is also recognized that the tissue cells may be pretreated with chemical compounds or radiation before injecting them into the joint space so that the cells stably express the gene of interest within the host organism. Preferably, the connective tissue cell does not cause a negative immune response when injected into the host organism. It is understood that allogeneic cells may be used in this regard, as well as autologous cells for cell-mediated gene therapy or somatic cell therapy.

As used herein, "connective tissue cell line" includes a plurality of connective tissue cells originating from a common parent cell.

As used herein, "decrease" of cells refers to a lessening of a population of cells compared with the amount that would normally be found at the site. This may mean a percentage reduction of a population of cells, such as at least 10%, 20%, 30%, 40%, 50%, 60%, 70%, 80%, or 90% compared with the normal cell population at the locus, or may mean damage or depletion of the cells at the locus.

As used herein, "helper cells" refer to those cells that are mixed with cells that are transfected or transduced with a gene of interest. The helper cells themselves are not transfected or transduced with the gene of interest. In particular, the cells transfected or transduced with the gene of interest generate protein that activates the helper cells. Administration of this mixture to a site of interest where the helper cells are endogenously made, but which are decreased at the time of administration, results in advantageously effective somatic gene therapy at the site of interest.

In one embodiment, "helper cells" may refer to connective tissue cells transfected or transduced with a gene encoding a member of the transforming growth factor β superfamily to form a mixture of cells. Such helper cells may include any connective tissue cells. Generally, these cells are not transfected or transduced with a gene encoding a member of the transforming growth factor β superfamily. In particular, these cells are not transfected or transduced with any gene, and these cells are generally resident in the cartilage area. Typically, the cell is a fibroblast or a chondrocyte.

As used herein, "histocompatibility" of a donor cell and recipient host refers to their sharing of a sufficient number of histocompatibility agents so that a transplantation is accepted and remains functional in the host mammal. In particular, the donor and recipient pair should be matched for Human Leukocyte Antigens (HLA), such as HLA type A, B, and C (Class I) and HLA type DR (Class II).

As used herein, "hyaline cartilage" refers to the connective tissue covering the joint surface. By way of example only, hyaline cartilage includes, but is not limited to, articular cartilage, costal cartilage, and nose cartilage.

In particular, hyaline cartilage is known to be self-renewing, responds to alterations, and provides stable movement with less friction. Hyaline cartilage found even within the same joint or among joints varies in thickness, cell density, matrix composition and mechanical properties, yet retains the same general structure and function. Some of the functions of hyaline cartilage include surprising stiffness to compression, resilience, and exceptional ability to distribute weight loads, ability to minimize peak stress on subchondral bone, and great durability.

Grossly and histologically, hyaline cartilage appears as a slick, firm surface that resists deformation. The extracellular matrix of the cartilage comprises chondrocytes, but lacks blood vessels, lymphatic vessels or nerves. An elaborate, highly ordered structure that maintains interaction between chondrocytes and the matrix serves to maintain the structure and function of the hyaline cartilage, while maintaining a low level of metabolic activity. The reference O'Driscoll, J. Bone Joint Surg., 80A: 1795-1812, 1998 describes the structure and function of hyaline cartilage in detail, which is incorporated herein by reference in its entirety.

As used herein, "injectable" composition refers to a composition that excludes various three-dimensional scaffold, framework, mesh or felt structure, which may be made of any material or shape that allows cells to attach to it and allows cells to grow in more than one layer, and which structure is generally implanted, and not injected. In one embodiment, the injection method of the invention is typically carried out by a syringe. However, any mode of injecting the composition of interest may be used. For instance, catheters, sprayers, or temperature dependent polymer gels also may be used.

As used herein, "mixed cell" or a "mixture of cells" or "cell mixture" refers to the combination of a plurality of cells that include a first population of cells that are transfected or transduced with a gene of interest that is expressed to benefit the helper cell, and which helper cells are the second population of cells.

In one embodiment of the invention, mixed cells may refer to the combination of a plurality of connective tissue cells that include cells that have been transfected or transduced with a gene or DNA encoding a member of the transforming growth factor β superfamily and helper cells that have not been transfected or transduced with a gene encoding a member of the transforming growth factor β superfamily. Typically, the ratio of cells that have not been transfected or transduced with a gene encoding a member of the transforming growth factor β superfamily to cells that have been transfected or transduced with a TGF superfamily gene may be in the range of about 3-20 to 1. The range may include about 3-10 to 1. In particular, the range may be about 10 to 1 in terms of the number of cells. However, it is understood that the ratio of these cells should not be necessarily fixed to any particular range so long as the combination of these cells is effective to produce hyaline cartilage in partially and fully defected joints.

As used herein, "pharmaceutically acceptable carrier" refers to any carrier that is known in the art to promote the efficiency of transport of the composition of the invention and prolong the effectiveness of the composition.

As used herein, "somatic cell" or "cell" in general refers to the cell of the body other than egg or sperm.

As used herein, "stored" cells refer to a composition of mixed cells that have been either stored individually or together before they are administered to the joint space. The cells may be stored in a refrigeration unit. Alternatively, the cells may be frozen at about −70' to about −196° C. in a liquid nitrogen tank or in an equivalent storage unit so that the cells are preserved for later administration into the joint space. The cells may be thawed using known protocols. The duration of freezing and thawing may be carried out by any number of ways, so long as the viability and potency of the cells are optimized.

As used herein, the terms "transfection" and "transduction" are mentioned as particular methods of transferring the DNA to the host cell and its subsequent integration into the recipient cell's chromosomal DNA. As the invention is practiced, any method transferring a foreign DNA to a host cell may be used, including nonviral or viral gene transfer methods, so long as a foreign gene is introduced into the host cell and the foreign gene is stably expressed in the host cell. Thus, as used herein, the term "transfected or transduced" includes any method of gene delivery to the cells, such as calcium phosphate precipitation, DEAE dextran, electroporation, liposome, viral mediation and so on.

As used herein, the "transforming growth factor-β (TGF-β) superfamily" encompasses a group of structurally related proteins, which affect a wide range of differentiation processes during embryonic development. The family includes, Müllerian inhibiting substance (MIS), which is required for normal male sex development (Behringer, et al., Nature, 345:167, 1990), Drosophila decapentaplegic (DPP) gene product, which is required for dorsal-ventral axis formation and morphogenesis of the imaginal disks (Padgett, et al., Nature, 325:81-84, 1987), the Xenopus Vg-1 gene product, which localizes to the vegetal pole of eggs (Weeks, et al., Cell, 51:861-867, 1987), the activins (Mason, et al., Biochem, Biophys. Res. Commun., 135:957-964, 1986), which can induce the formation of mesoderm and anterior structures in Xenopus embryos (Thomsen, et al., Cell, 63:485, 1990), and the bone morphogenetic proteins (BMP's, such as BMP-2, 3, 4, 5, 6 and 7, osteogenin, OP-1) which can induce de novo cartilage and bone formation (Sampath, et al., J. Biol. Chem., 265:13198, 1990). The TGF-β gene products can influence a variety of differentiation processes, including adipogenesis, myogenesis, chondrogenesis, hematopoiesis, and epithelial cell differentiation. For a review, see Massague, Cell 49:437, 1987, which is incorporated herein by reference in its entirety.

The proteins of the TGF-β family are initially synthesized as a large precursor protein, which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., Nature, 321:779, 1986) and the TGF-β's (Cheifetz, et al., Cell, 48:409, 1987), heterodimers have also been detected, and these appear to have different biological properties than the respective homodimers.

Members of the superfamily of TGF-β genes include TGF-β3, TGF-β2, TGF-β4 (chicken), TGF-β1, TGF-β5 (Xenopus), BMP-2, BMP-4, Drosophila DPP, BMP-5, BMP-6, Vgr1, OP-1/BMP-7, Drosophila 60A, GDF-1, Xenopus Vgf, BMP-3, Inhibin-βA, Inhibin-βB, Inhibin-α, and MIS. These genes are discussed in Massague, Ann. Rev. Biochem. 67:753-791, 1998, which is incorporated herein by reference in its entirety.

Preferably, the member of the superfamily of TGF-β genes is TGF-β and BMP. More preferably, the member is TGF-β1, TGF-β2, TGF-β3, BMP-2, BMP-3, BMP-4, BMP-5, BMP-6, or BMP-7. Most preferably, the member is human or porcine TGF-β1 or BMP-2.

As used herein, "selectable marker" includes a gene product that is expressed by a cell that stably maintains the introduced DNA, and causes the cell to express an altered phenotype such as morphological transformation, or an enzymatic activity. Isolation of cells that express a transfected or transduced gene is achieved by optional introduction into the same cells a second gene that encodes a selectable marker, such as one having an enzymatic activity that confers resistance to an antibiotic or other drug.

Examples of selectable markers include, but are not limited to, thymidine kinase, dihydrofolate reductase, aminoglycoside phosphotransferase, which confers resistance to aminoglycoside antibiotics such as kanamycin, neomycin and geneticin, hygromycin B phosphotransferase, xanthine-guanine phosphoribosyl transferase, CAD (a single protein that possesses the first three enzymatic activities of de novo uridine biosynthesis—carbamyl phosphate synthetase, aspartate transcarbamylase and dihydroorotase), adenosine deaminase, and asparagine synthetase (Sambrook et al. Molecular Cloning, Chapter 16. 1989), incorporated herein by reference in its entirety. It is understood that using a selectable marker is not a requirement to practice the claimed invention. In fact, in one embodiment, a selectable marker is not incorporated into the genetic construct of the claimed invention.

As used herein, a "promoter" can be any sequence of DNA that is active, and controls transcription in an eucaryotic cell. The promoter may be active in either or both eucaryotic and procaryotic cells. Preferably, the promoter is active in mammalian cells. The promoter may be constitutively expressed or inducible. Preferably, the promoter is inducible. Preferably, the promoter is inducible by an external stimulus. More preferably, the promoter is inducible by hormones or metals. Most preferably, the promoter is a metallothionein gene promoter or a promoter inducible by glucocorticoids. Likewise, "enhancer elements", which also control transcription, can be inserted into the DNA vector construct, and used with the construct of the present invention to enhance the expression of the gene of interest.

As used herein, the term "DC-chol" means a cationic liposome containing cationic cholesterol derivatives. The "DC-chol" molecule includes a tertiary amino group, a medium length spacer arm (two atoms) and a carbamoyl linker bond (Gao et al., Biochem. Biophys. Res, Commun., 179:280-285, 1991).

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

The present invention encompasses administering a mixture of cells to a site in need thereof in a mammal, wherein the first population of cells is transfected or transduced with a gene of interest to be expressed at the site of intererest in a mammal. As somatic gene therapy is attempted, the present invention provides for including a second population of cells that are not transfected or transduced with the gene of interest, and which cells are endogenously decreased at the wounded or diseased or otherwise debilitated site of interest, thus requiring activation by expression of the gene of interest at the site of interest together with the second population of cells to thus activate and grow the cells of the second population type that are either endogenously made or exogenously administered.

In particular, the present invention discloses ex vivo and in vivo techniques for delivery of a DNA sequence of interest to the connective tissue cells of the mammalian host. The ex vivo technique involves culture of target connective tissue cells, in vitro transfection or transduction of the DNA sequence, DNA vector or other delivery vehicle of interest into the connective tissue cells, followed by transplantation of the modified connective tissue cells to the target joint of the mammalian host, so as to effect in vivo expression of the gene product of interest.

It is to be understood that while it is possible that substances such as a scaffolding or a framework as well as various extraneous tissues may be implanted together in the gene therapy protocol of the present invention, it is also possible that such scaffolding or tissue not be included in the injection system of the invention. In a preferred embodiment, in a cell-mediated gene therapy or somatic cell therapy, the invention is directed to a simple method of injecting a population of transfected or transduced connective tissue cells to the joint space so that the exogenous TGF superfamily protein is expressed in the joint space.

One ex vivo method of treating a connective tissue disorder disclosed throughout this specification comprises initially generating a recombinant viral or plasmid vector which contains a DNA sequence encoding a protein or biologically active fragment thereof. This recombinant vector is then used to infect or transfect a population of in vitro cultured connective tissue cells, resulting in a population of connective cells containing the vector. These connective tissue cells are then transplanted to a target joint space of a mammalian host either as a mixture or separately into the joint space so as to cause a mixture inside the joint, thus effecting subsequent expression of the protein or protein fragment within the joint space. Expression of this DNA sequence of interest is useful in substantially reducing at least one deleterious joint pathology associated with a connective tissue disorder.

It will be understood by the artisan of ordinary skill that the source of cells for treating a human patient may be the patient's own connective tissue cells, such as autologous fibroblast or chondrocyte cells, but that allogeneic cells as well as xenogeneic cells may also be used without regard to the histocompatibility of the cells. Alternatively, in one embodiment of the invention, allogeneic cells may be used having matching histocompatibility to the mammalian host. To describe in further detail, the histocompatibility of the donor and the patient are determined so that histocompatible cells are administered to the mammalian host.

More specifically, this method includes employing as the gene a gene capable of encoding a member of the transforming growth factor β superfamily, or a biologically active derivative or fragment thereof and a selectable marker, or a biologically active derivative or fragment thereof.

A further embodiment of the present invention includes employing as the gene a gene capable of encoding at least one member of the transforming growth factor β superfamily or a biologically active derivative or fragment thereof, and employing as the DNA plasmid vector any DNA plasmid vector known to one of ordinary skill in the art capable of stable maintenance within the targeted cell or tissue upon delivery, regardless of the method of delivery utilized.

Another embodiment of this invention provides a method for introducing at least one gene encoding a product into at least one cell of a connective tissue for use in treating the mammalian host. This method includes employing non-viral means for introducing the gene coding for the product into the connective tissue cell. More specifically, this method includes a liposome encapsulation, calcium phosphate coprecipitation, electroporation, or DEAE-dextran mediation, and includes employing as the gene a gene capable of encoding a member of transforming growth factor superfamily or biologically active derivative or fragment thereof, and a selectable marker, or biologically active derivative or fragment thereof.

Another embodiment of this invention provides an additional method for introducing at least one gene encoding a product into at least one cell of a connective tissue for use in treating the mammalian host. This additional method includes employing the biologic means of utilizing a virus to deliver the DNA vector molecule to the target cell or tissue. Preferably, the virus is a pseudo-virus, the genome having been altered such that the pseudovirus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue.

A preferred embodiment of the invention is a method of delivering TGF-β or BMP to a target joint space by delivering the TGF-β or BMP gene to the connective tissue of a mammalian host through use of a retroviral vector with the ex vivo technique disclosed within this specification. In other words, a DNA sequence of interest encoding a functional TGF-β or BMP protein or protein fragment is subcloned into a retroviral transfer vector of choice. The recombinant retroviruses are produced in packaging cells and then grown to adequate titer and used to infect in vitro cultured connective tissue cells. The transduced connective tissue cells, preferably autografted cells, are transplanted into the joint of interest combined with a non-transfected or -transduced sample of connective tissue cell such as chondrocytes preferably by intra-articular injection.

Another preferred method of the present invention involves direct in vivo delivery of a TGF-β superfamily gene to the connective tissue of a mammalian host through use of either a retroviral vector, adenovirus vector, adeno-associated virus (AAV) vector or herpes-simplex virus (HSV) vector. In other words, a DNA sequence of interest encoding a functional TGF-β or BMP protein or protein fragment is subcloned into the respective viral vector. The TGF-β or BMP containing recombinant virus is then grown to adequate titer and directed into the joint space, preferably by intra-articular injection.

Methods of presenting the DNA molecule to the target connective tissue of the joint includes, but is not limited to, encapsulation of the DNA molecule into cationic liposomes, subcloning the DNA sequence of interest in a retroviral or plasmid vector, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the connective tissue.

In a preferred embodiment, fibroblasts and chondrocytes are cultured in vitro for subsequent utilization as a delivery system for gene therapy. It will be apparent that Applicants are not limited to the use of the specific connective tissue disclosed. It would be possible to utilize other tissue sources for in vitro culture techniques. The method of using the gene of this invention may be employed both prophylactically and in the therapeutic treatment of osteoarthritis and wound healing. It will also be apparent that the invention is not limited to prophylactic or therapeutic applications for treating only the knee joint. It would be possible to utilize the present invention either prophylactically or therapeutically to treat osteoarthritis in any susceptible joint or any damage resulting from an injury caused by a tear or degradation of the cartilage.

In another embodiment of this invention, a compound for parenteral administration to a patient in a therapeutically effective amount is provided that contains a gene encoding a TGF-β superfamily protein and a suitable pharmaceutical carrier.

Another embodiment of this invention provides for a compound for parenteral administration to a patient in a prophylactically effective amount that includes a gene encoding a TGF-β superfamily protein and a suitable pharmaceutical carrier.

In a further embodiment of this invention the cells are stored before administration to the joint space. The transfected or transduced cells alone may be stored, or the untransfected helper cells alone may be stored, or the mixture may be stored, but not necessarily simultaneously. In addition, the duration of storage need not be for the same time period. Thus, the individually stored cells may be mixed prior to injection. Alternatively, the cells may be stored and injected separately to form a mixture of cells within the joint space. It will be appreciated by those skilled in the art that these cells may be stored frozen in a cryopreservative such as but not limited to a composition of about 10 percent DMSO in liquid nitrogen or an equivalent storage medium.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene encoding for the product directly into the mammalian host. Preferably, this method includes effecting the direct introduction into the mammalian host by intra-articular injection. This method includes employing the method to substantially prevent a development of arthritis in a mammalian host having a high susceptibility of developing arthritis. This method also includes employing the method on an arthritic mammalian host for therapeutic use. Further, this method also includes employing the method to repair and regenerate the connective tissue as hereinbefore defined.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding a member belonging to the TGF-β superfamily and optionally with a selectable marker gene, such as an antibiotic resistance gene. And it is also understood that a selectable marker gene is not a requirement to practicing the claimed invention.

Another embodiment of the present invention is delivery of a DNA sequence encoding a member of the TGF-β superfamily to the connective tissue of a mammalian host by any of the methods disclosed within this specification so as to effect in vivo expression of collagen to regenerate connective tissue, such as cartilage.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of proteins to joints provides direct access to a joint. However, most of the injected drugs in the form of encapsulated proteins have a short intra-articular half-life. The present invention solves these problems by introducing into the connective tissue of a mammalian host genes coding for proteins that may be used to treat the mammalian host. More specifically, this invention provides a method for introducing into the connective tissue of a mammalian host genes coding for proteins with anti-arthritic properties.

In the Examples provided herein, NIH3T3-TGF-β1 and NIH3T3-BMP-2 cells mixed with untransduced chondrocyte helper cells stimulated collagen synthesis in the joint. In the Examples, the joint was injected with $2\times10^6$ cells/ml concentration of a mixture of NIH3T3-TGF-β1 or NIH3T3-BMP-2 cells and untransduced chondrocyte helper cells at a 1:10 ratio of transfected cells to helper cells. The specimens were harvested from 6 weeks to 12 weeks after injection. The cells move freely within the joint, and move to the area with specific affinity for these cells. The synovium, meniscus and cartilage defect areas may be possible sites for cellular adhesion. At six and twelve weeks after injection, the regenerated tissues were observed in both the partially and completely damaged cartilage defect areas. This specific affinity for the damaged area is another advantage of using mixed cells for clinical application. If degenerative arthritis can be cured with just injection of cells into the joint without including various physical apparatuses such as scaffolding or any other three-dimensional structure, the patients can be treated conveniently without major surgery.

Whatever the mechanism of action is, and without being bound to any particular theory regarding the mechanism of action, the finding of hyaline cartilage synthesis by using the mixed cell composition of the invention indicates that a long duration of high TGF-β or BMP concentration can stimulate hyaline cartilage regeneration. The properties of newly formed tissue were determined by histological methods. Through Mason's trichrome staining and Safranin-O, it was indicated that the newly formed tissue was identical to the surrounding hyaline cartilage (FIGS. 3 through 7).

The following examples are offered by way of illustration of the present invention, and not by way of limitation.

EXAMPLES

Example I

Materials and Methods

Plasmid Construction

The plasmid pMTMLVβ1 was generated by subcloning a 1.2-kb Bgl II fragment containing the TGF-β1 coding sequence and a growth hormone poly A site at the 3' end into the Bam HI site of pMTMLV. The plasmid pMTBMP2 was generated by subcloning a 1.2-kb Sal I-Not I fragment containing the BMP2 coding sequence into the Sal I-Not I sites of pMTMLV. pMTMLV vector was derived from the retroviral vector MFG by deleting entire gag and env sequences as well as some of ψ packaging sequence.

Cell Culture and Transduction—The TGF-β and BMP-2 cDNA cloned in retroviral vectors were individually transduced into fibroblasts (NIH3T3-TGF-β1 and NIH3T3-BMP-2) and chondrocytes (hChon-TGF-β1). They were cultured in Dulbecco's Modified Eagle's Medium (GIBCO-BRL, Rockville, Md.) with 10% concentration of fetal bovine serum.

To select the cells with the transduced gene sequence, neomycin (300 μg/ml) was added into the medium. The cells with TGF-β1 and BMP-2 expression were sometimes stored in liquid nitrogen and cultured just before the injection.

TGF-β gene transfection was carried out by using the calcium phosphate coprecipitation method (FIG. 1). About 80% of the surviving colonies expressed the transgene mRNA. These selected TGF-β1-producing cells were incubated in a zinc sulfate solution. When the cells were cultured in 100 mM zinc sulfate solution, they produced mRNA. The TGF-β secretion rate was about 32 ng/$10^6$ cells/24 hr.

Figure 2:
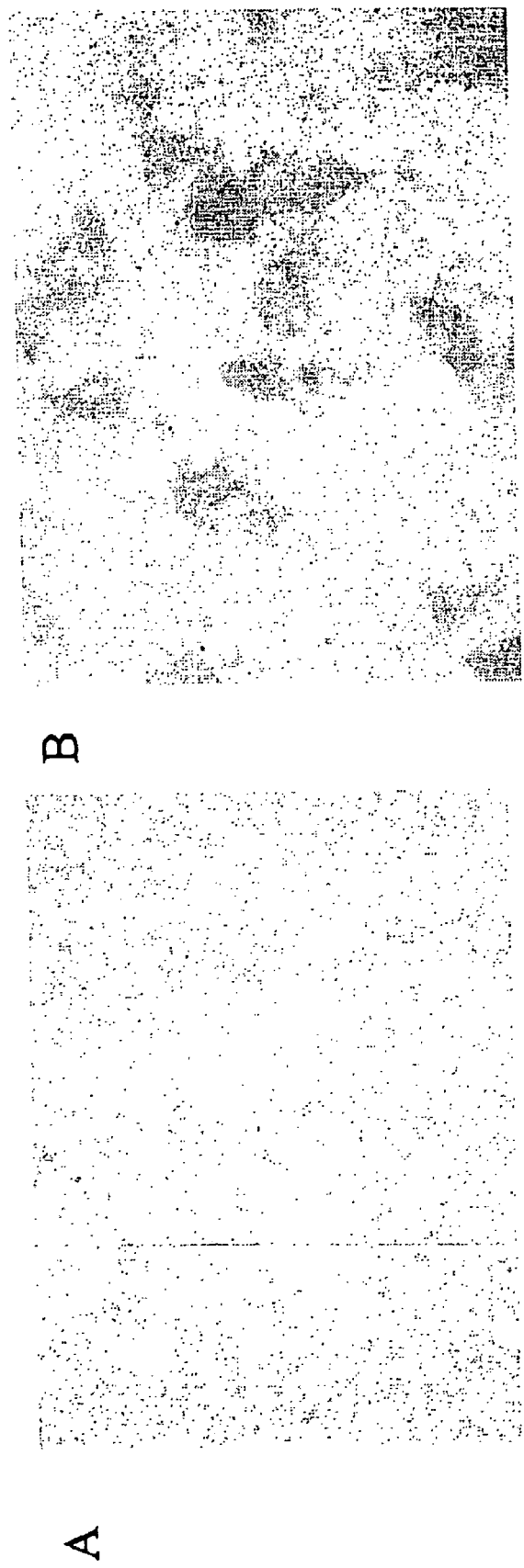
FIGS. 2A and 2B show expression of BMP2 in NIH3T3-BMP2 cells.
Figure 3:
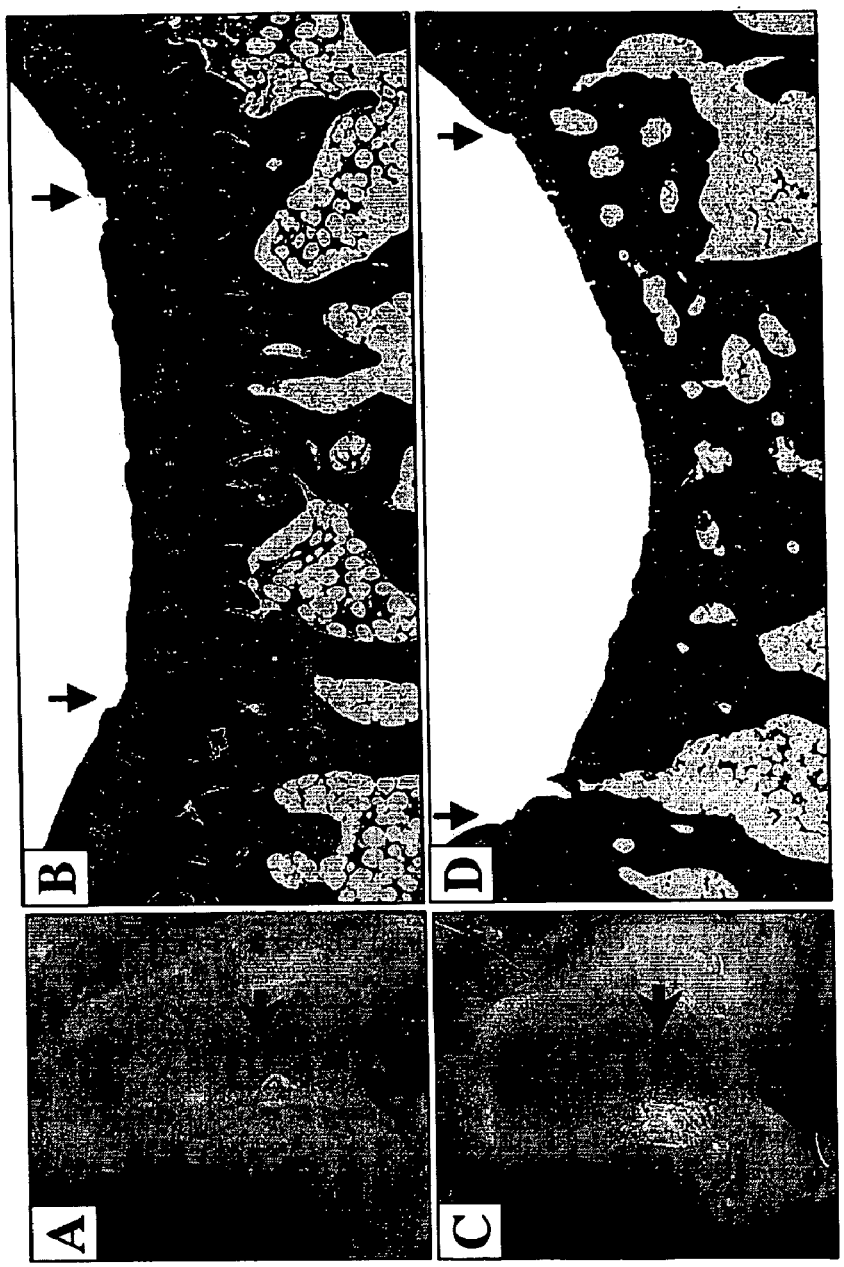
FIGS. 3A-3D show regeneration of cartilage with mixed-cell (human chondrocytes and NIH3T3-TGF-β1 cells) injection in rabbits with a partial defect.
Figure 4:
FIGS. 4A-4E show regeneration of cartilage with mixed-cell (human chondrocytes and NIH3T3-TGF-β1 cells) injection in rabbits with a full-thickness defect.
Figure 5:
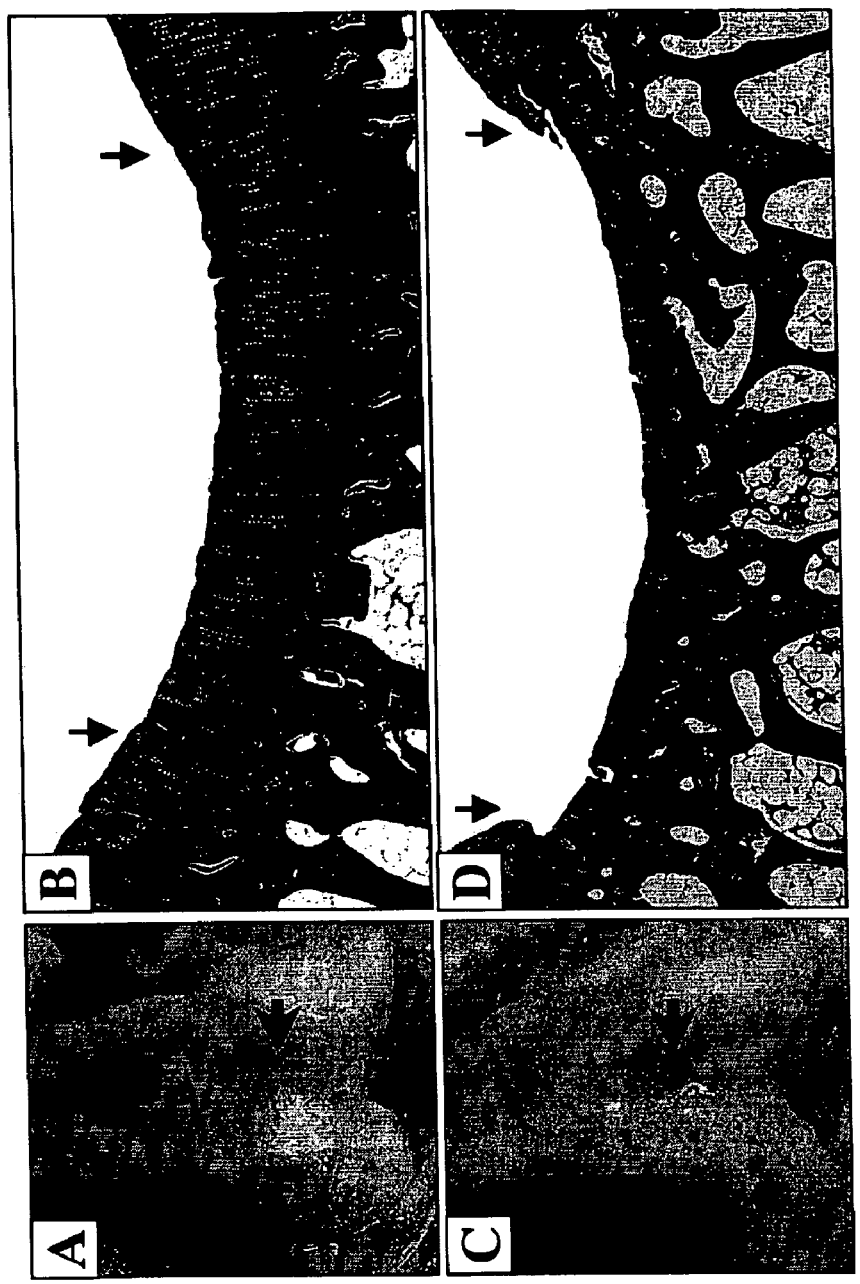
FIGS. 5A-5D show regeneration of cartilage with mixed-cell (human chondrocytes and NIH3T3-BMP-2 cells) injection in rabbits with a partial defect.
Figure 6:
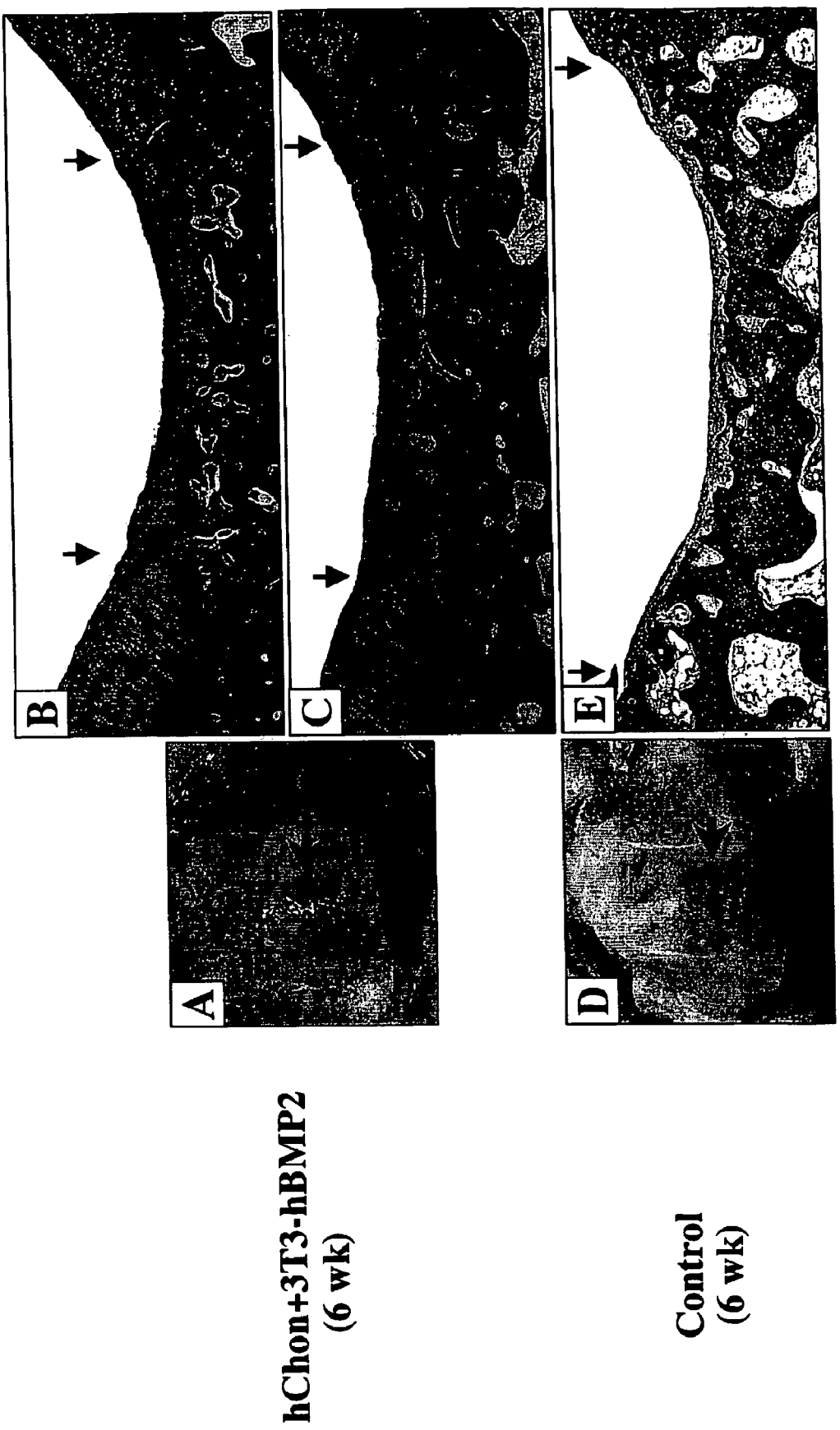
FIGS. 6A-6E show regeneration of cartilage with mixed-cell (human chondrocytes and NIH3T3-BMP-2 cells) injection in rabbits with a full-thickness defect.
Figure 7:
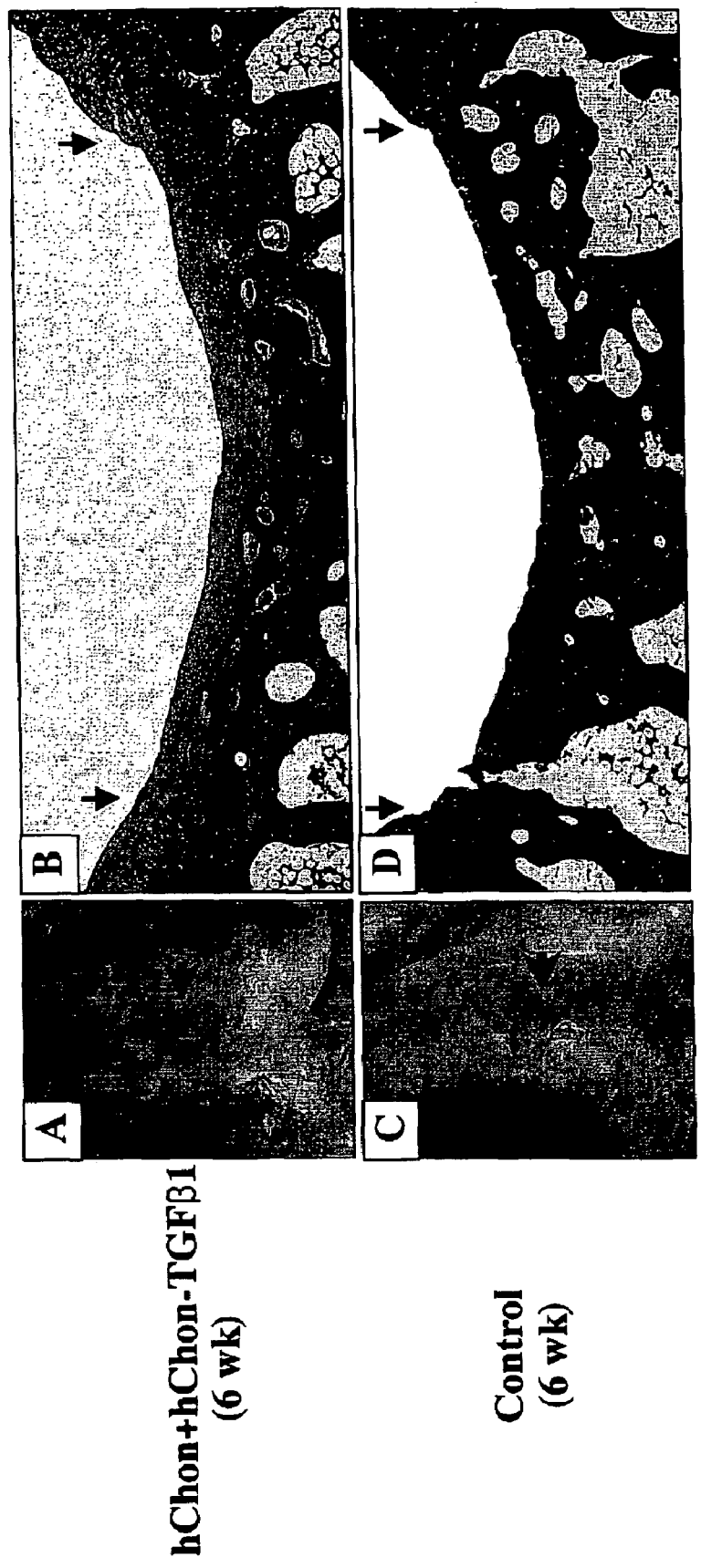
FIGS. 7A-7D show regeneration of cartilage with mixed-cell (human chondrocytes and human chondrocyte-TGF-β1 cells) injection in rabbits with a full-thickness defect.

To test and confirm the production of biologically active BMP2 proteins by NIH3T3 fibroblast cells infected with retroviral vectors containing BMP2 cDNAs, alkaline phosphatase (ALP) activity assays were carried out with control NIH3T3-methallothionein (FIG. 2A) and NIH3T3-BMP2 cells (FIG. 2B). Blue color in FIG. 2B shows expression of BMP2 protein.

$1.5\times10^6$ NIH3T3 cells were grown overnight in a 6 well tissue culture plate. $0.5\times10^5$ indicating cells (MC3T3E1) were placed in tissue culture inserts and grown overnight. Culture medium was aspirated from the culture insert and the culture insert transferred into a 6 well plate and incubated for 48-72 hours. Culture medium was aspirated from the culture inserts. 5 ml of 1× phosphate buffered saline (PBS) was added to wash the cells. 4 ml of 3.7% formaldehyde/1×PBS solution was added to each insert, and the cells were fixed for 20 min at 4° C. Cells were washed twice with 1×PBS. 3 ml of ALP staining solution was added to each culture insert, and the culture insert was incubated for about 20 min to 1 hr at room temperature in the dark for blue color development. ALP staining solution is 0.1 mg/ml naphthol AS-MX phosphate (Sigma N5000), 0.5%, N-dimethylformamide (Sigma D8654), 2 mM $MgCl_2$, 0.3 mg/ml Fast Blue BB salt (Sigma F3378) in 0.1 M Tris-HCl, pH 8.5.

Example II

Experimental Methods and Results

Regeneration of Rabbit Articular Cartilage Defect—New Zealand white rabbits weighing 2.0-2.5 kg were selected for the animal study. These rabbits were mature and had a tidemark. The knee joint was exposed and a partial cartilage defect (3 mm×6 mm, 1-2 mm deep) or full-thickness defect (3 mm×6 mm, 2-3 mm deep) was made on the hyaline cartilage layer of the femoral condyle with a surgical knife. Either control human chondrocytes (hChon), or mixture of hChon and NIH3T3-TGF-β1 cells, or NIH3T3-BMP-2 cells were injected into the rabbit knee joint with the defect. These cells (15-20 μl of $2\times10^6$ cells/ml) were loaded to the top of the defect and then left in the defect for 15-20 min to allow the cells to permeate the wound before suturing. In the experiment in which mixtures of hChon and NIH3T3-BMP-2 cells were injected into rabbits with full-thickness defect, these mixed cell compositions were injected into the defect 3 weeks after making the defect. The femoral condyles were harvested at 6 or 12 weeks post injection of the cells and examined.

Regeneration Of Cartilage With Mixed-Cell (Human Chondrocytes And NIH3T3-TGF-β1 Cells) Injection In Rabbits With A Partial Defect—Either control hChon or a composition comprising a mixture of hChon and NIH3T3-TGF-β1 cells was injected into the rabbit knee joint containing a partial cartilage defect (3 mm×5 mm, 1-2 mm deep) on the femoral condyle. The mixture of cells (15-20 μl of $2\times10^6$ cells/ml, 10:1 ratio of hChon and NIH3T3-TGF-β1) was loaded to the top of the defect and then left in the defect for 15-20 min to allow the cells to permeate the wound before suturing. The specimens were harvested at 6 weeks after injection and observed microscopically. FIGS. 3A and 3C show pictures of the femoral condyles 6 weeks post injection with either a mixture of hChon and NIH3T3-TGF-β1 cells (A) or hChon alone (C). FIGS. 3B and 3D show Mason's trichrome staining of sections from the femoral condyle injected with either a mixture of hChon and NIH3T3-TGF-β1 cells (B) or hChon alone (D). [Original magnification: (B & D)×12.5].

Regeneration Of Cartilage With Mixed-Cell (Human Chondrocytes And NIH3T3-TGF-β1 Cells) Injection In Rabbits With A Full-Thickness Defect—Either control hChon or a mixture of hChon and NIH3T3-TGF-β1 cells was injected into the rabbit knee joint containing a full-thickness cartilage defect (3 mm×5 mm, 2-3 mm deep) on the femoral condyle. The cell mixture (20-25 μl of $2\times10^6$ cells/ml, 10:1 ratio of hChon and NIH3T3-TGF-β1) was loaded to the top of the defect and then left in the defect for 15-20 min to allow the cells to permeate the wound before suturing. The specimens were harvested at 12 weeks after injection and observed microscopically. FIGS. 4A and 4D show pictures of the femoral condyles 12 weeks post injection with either a mixture of hChon and NIH3T3-TGF-β1 cells (A) or hChon alone (D). FIGS. 4B, 4C and 4E show Mason's trichrome staining (B and E) and Safranin-O staining (C) of sections from the femoral condyle injected with either mixture of hChon and NIH3T3-TGF-β1 cells (B and C) or hChon alone (E). [Original magnification: (B, C & E)×12.5].

Regeneration Of Cartilage With Mixed-Cell (Human Chondrocytes And NIH3T3-BMP-2 Cells) Injection In Rabbits With A Partial Defect—Either control hChon or a mixture of hChon and NIH3T3-BMP-2 cells were injected into the rabbit knee joint containing a partial cartilage defect (3 mm×5 mm, 1-2 mm deep) on the femoral condyle. The cell mixture (15-20 μl of $2\times10^6$ cells/ml, 10:1 ratio of hChon and NIH3T3-BMP-2) was loaded to the top of the defect and then left in the defect for 15-20 min to allow the cells to permeate the wound before suturing. The specimens were harvested at 6 weeks after injection and observed microscopically. FIGS. 5A and 5C show pictures of the femoral condyles 6 weeks post injection with either mixture of hChon and NIH3T3-BMP-2 cells (A) or hChon alone (C). FIGS. 5B and 5D show Mason's trichrome staining of sections from the femoral condyle injected with either mixture of hChon and NIH3T3-BMP-2 cells (B) or hChon alone (D). [Original magnification: (B and D)×12.5].

Regeneration Of Cartilage With Mixed-Cell (Human Chondrocytes And NIH3T3-BMP-2 Cells) Injection In Rabbits With A Full-Thickness Defect—Either control hChon or a mixture of hChon and NIH3T3-BMP-2 cells was injected into the rabbit knee joint containing a full-thickness cartilage defect (3 mm×5 mm, 2-3 mm deep) on the femoral condyle. In this case, the cells were injected 3 weeks after making the defect. The cell mixture (20-25 μl of $2\times10^6$ cells/ml, 10:1 ratio of hChon and NIH3T3-BMP-2) was loaded to the top of the defect and then left in the defect for 15-20 min to allow the cells to permeate the wound before suturing. The specimens were harvested at 6 weeks after injection and observed microscopically. FIGS. 6A and 6D show pictures of the femoral condyles 12 weeks post injection with either a mixture of hChon and NIH3T3-BMP-2 cells (A) or hChon alone (D). FIGS. 6B, 6C and 6E show Mason's trichrome staining (B and E) and Safranin-O staining (C) of sections from the femoral condyle injected with either a mixture of hChon and NIH3T3-BMP-2 cells (B and C) or hChon alone (E). [Original magnification: (B, C and E)×12.5].

Regeneration Of Cartilage With Mixed-Cell (Human Chondrocytes And Human Chondrocyte-TGF-β1 Cells) Injection In Rabbits With A Full-Thickness Defect—Either control human chondrocytes (hChon) or a mixture of hChon and hChon-TGF-β1 cells was injected into the rabbit knee joint containing a full-thickness cartilage defect (3 mm×5 mm, 2-3 mm deep) on the femoral condyle. The cell mixture (20-25 μl of $2\times10^6$ cells/ml, 1:1 ratio of hChon and hChon-TGF-β1) was loaded to the top of the defect and then left in the defect for 15-20 min to allow the cells to permeate the wound before suturing. The specimens were harvested at 6 weeks after injection and observed microscopically. FIGS. 7A and 7C show pictures of the femoral condyles 6 weeks post injection with either a mixture of hChon and hChon-TGF-β1 cells (A) or hChon alone (C). FIGS. 7B and 7D show Mason's trichrome staining of sections from the femoral condyle injected with either mixture of hChon and hChon-TGF-β1 cells (B) or hChon alone (D). [Original magnification: (B& D)×12.5].

Figure 8:
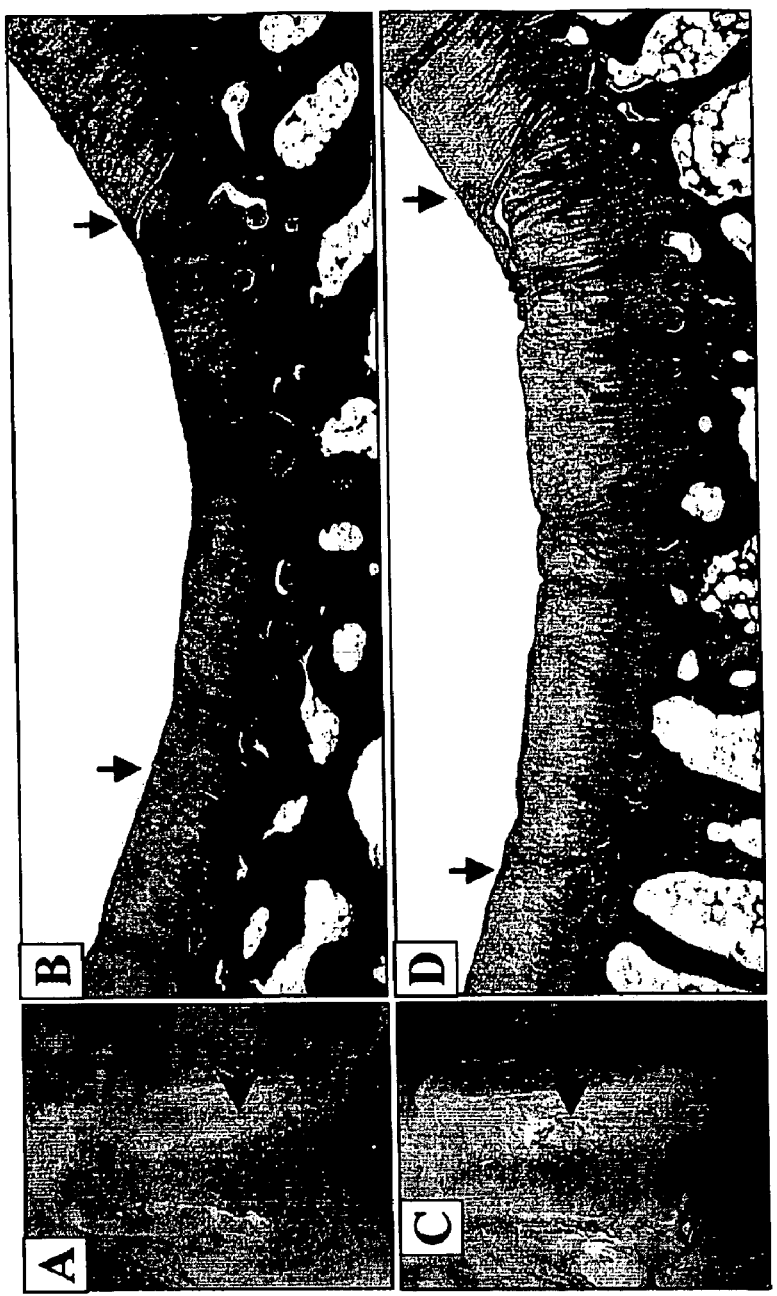
FIGS. 8A-8D show regeneration of cartilage with mixed-cell (human chondrocytes and human chondrocyte-TGF-β1 Cells) injection in rabbits with a partial defect.

Regeneration Of Cartilage With Mixed-Cell (Human Chondrocytes And Human Chondrocyte-TGF-β1 Cells) Injection In Rabbits With A Partial Defect—A mixture of hChon and hChon-TGF-β1 cells was injected into the rabbit knee joint containing a partial cartilage defect (3 mm×5 mm, 1-2 mm deep) on the femoral condyle. The cell mixture (15-20 μl of $2\times10^6$ cells/ml, 3:1 or 5:1 ratio of hChon and hChon-TGF-β1) was loaded to the top of the defect and then left in the defect for 15-20 min to allow the cells to permeate the wound before suturing. The specimens were harvested at 6 weeks after injection and observed microscopically. FIGS. 8A and 8C show pictures of the femoral condyles 6 weeks post injection with a mixture of hChon and hChon-TGF-β1 cells (3:1 ratio) (A) or a mixture of hChon and hChon-TGF-β1 cells (5:1 ratio) (C). FIGS. 8B and 8D show Mason's trichrome staining of sections from the femoral condyle injected with a mixture of hChon and hChon-TGF-β1 cells with 3:1 ratio (B) or 5:1 (D). [Original magnification: (B&D)×12.5].

All of the references cited herein are incorporated by reference in their entirety.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A mixed cell composition to generate hyaline cartilage at a target site, comprising
   a) a first population of fibroblast or chondrocyte cells transfected or transduced with a gene encoding transforming growth factor β1 (TGF-β1) or bone morphogenetic protein 2 (BMP-2);
   b) a second population of chondrocyte cells that have not been transfected or transduced with said gene, wherein endogenously existing forms of chondrocyte cells are decreased at the target site, and wherein generation of TGF-β1 or BMP-2 by the first population of fibroblast or chondrocyte cells at the target site stimulates the second population of chondrocyte cells to generate hyaline cartilage; and c) a pharmaceutically acceptable carrier thereof, wherein the ratio of the second population of chondrocyte cells that have not been transfected or transduced with the gene encoding TGF-β1 or BMP-2 to the first population of fibroblast or chondrocyte cells that have been transfected or transduced with a gene encoding TGF-β1 or BMP-2 in the composition is 1-20 to 1.

2. The mixed cell composition according to claim 1, wherein said composition is an injectable composition.

3. The composition according to claim 1, comprising hyaline cartilage-generating effective amount of,
   a) a first population of chondrocyte cells transfected or transduced with a gene encoding TGF-β1 or BMP-2;
   b) a second population of chondrocyte cells that have not been transfected or transduced with the gene encoding TGF-β1 or BMP-2, wherein endogenously existing forms of chondrocyte cells are decreased at the target site, and wherein generation of TGF-β1 or BMP-2 by the first population of chondrocyte cells at the target site stimulates the second population of chondrocyte cells to generate hyaline cartilage; and
   c) a pharmaceutically acceptable carrier thereof,
   wherein the ratio of the second population of chondrocyte cells that have not been transfected or transduced with a gene encoding TGF-β1 or BMP-2 to the first population of or chondrocyte cells that have been transfected or transduced with a gene encoding TGF-β1 or BMP-2 in the composition is 1-20 to 1.

4. The composition according to claim 1, wherein said ratio is 1-10 to 1.

5. The composition according to claim 4, wherein said ratio is 1-3 to 1.

6. The composition according to claim 1, wherein the first population of fibroblast or chondrocyte cells transfected or transduced with a gene encoding TGF-β1 or BMP-2 is irradiated.

7. The composition according to claim 1, wherein the first population of fibroblast or chondrocyte cells transfected or transduced with a gene encoding TGF-β1 or BMP-2 and the second population of chondrocyte cells not transfected or transduced with the gene encoding TGF-β1 or BMP-2 are obtained from the same source mammal.

8. The composition according to claim 1, wherein the first population of fibroblast or chondrocyte cells transfected or transduced with a gene encoding TGF-β1 or BMP-2 and the second population of chondrocyte cells not transfected or transduced with the gene encoding TGF-β1 or BMP-2 are obtained from different source mammals.

9. An injectable mixed cell composition comprising a hyaline cartilage-generating effective amount of,
   a) a first population of fibroblast or chondrocyte cells transfected or transduced with a gene encoding transforming growth factor β1 (TGF-β1) or bone morphogenic protein 2 (BMP-2);
   b) a second population of chondrocyte cells that have not been transfected or transduced with the gene encoding TGF-β1 or BMP-2; and
   c) a pharmaceutically acceptable carrier thereof,
   wherein the ratio of the second population of chondrocyte cells that have not been transfected or transduced with a gene encoding TGF-β1 or BMP-2 to the first population of fibroblast or chondrocyte cells that have been transfected or transduced with a gene encoding TGF-β1 or BMP-2 in the composition is about 1-20 to 1.

10. A storage container for storing cells at a temperature of about −70° C. to about −196° C., comprising a mixed cell composition according to claim 1.

11. A storage container for storing cells at a temperature of about −7° C. to about −196° C., comprising the composition according to claim 2.

12. A storage container for storing cells at a temperature of about −7° C. to about −196° C., comprising the composition according to claim 3.

13. A storage container for storing cells at a temperature of about −7° C. to about −196° C., comprising the composition according to claim 4.

14. A storage container for storing cells at a temperature of about −7° C. to about −196° C., comprising the composition according to claim 5.

15. A storage container for storing cells at a temperature of about −7° C. to about −196° C., comprising the composition according to claim 6.

16. A storage container for storing cells at a temperature of about −7° C. to about −196° C., comprising the composition according to claim 7.

17. A storage container for storing cells at a temperature of about −7° C. to about −196° C., comprising the composition according to claim 8.

* * * * *